(12) United States Patent
Tanaka

(10) Patent No.: US 8,306,301 B2
(45) Date of Patent: Nov. 6, 2012

(54) IMAGE PROCESSING APPARATUS AND IMAGE PROCESSING METHOD

(75) Inventor: Kenichi Tanaka, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/237,113

(22) Filed: Sep. 20, 2011

(65) Prior Publication Data

US 2012/0121144 A1    May 17, 2012

Related U.S. Application Data

(63) Continuation of application No. PCT/JP2011/058315, filed on Mar. 31, 2011.

(30) Foreign Application Priority Data

Jul. 21, 2010   (JP) .................. 2010-164238

(51) Int. Cl.
*G06K 9/00* (2006.01)
(52) U.S. Cl. ........ 382/128; 382/199; 382/130; 382/131; 600/437; 600/443
(58) Field of Classification Search .................. 382/128, 382/199, 130, 131; 600/437, 443
See application file for complete search history.

(56) References Cited

U.S. PATENT DOCUMENTS

| 6,600,832 B1 | 7/2003 | Nakayama et al. |
| 2004/0197015 A1 * | 10/2004 | Fan et al. ................ 382/128 |

FOREIGN PATENT DOCUMENTS

| JP | 10-143648 | 5/1998 |
| JP | 2000-316097 | 11/2000 |
| JP | 2008-194334 | 8/2008 |

* cited by examiner

*Primary Examiner* — Matthew Bella
*Assistant Examiner* — Ruiping Li
(74) *Attorney, Agent, or Firm* — Scully, Scott, Murphy & Presser, PC

(57) ABSTRACT

An image processing apparatus includes: a region detection section which detects a candidate region in which a structure having a predetermined shape is estimated to exist from an image a border pixel detection section which detects a border of the candidate region; a region setting section which sets a local region in the vicinity of and both sides of the border; a feature value calculation section which calculates predetermined feature values based on predetermined values obtained for respective pixel units of the local regions; a discrimination value calculation section which calculates a discrimination value based on calculation results of the predetermined feature values in local region groups on one side and the other side when viewed from the border; and a candidate region correction section which corrects a detection result of a candidate region based on a calculation result of the discrimination value.

20 Claims, 12 Drawing Sheets

IMAGE PROCESSING APPARATUS AND IMAGE PROCESSING METHOD

CROSS REFERENCE TO RELATED APPLICATION

This application is a continuation application of PCT/JP2011/058315 filed on Mar. 31, 2011 and claims benefit of Japanese Application No. 2010-164238 filed in Japan on Jul. 21, 2010, the entire contents of which are incorporated herein by this reference.

BACKGROUND OF THE INVENTION

1. Field of the Invention

The present invention relates to an image processing apparatus and an image processing method, and more particularly to an image processing apparatus and an image processing method used for diagnosis of living tissues and the like.

2. Description of the Related Art

In recent years, for the purpose of supporting to identify a lesion site (abnormal site) in an image obtained by picking up an image of a living tissue in a body cavity using an endoscope and the like, studies have been developed on an image processing for detecting a running pattern of a blood vessel under a living mucosa and (or) a predetermined structure of an epithelial tissue from the obtained image.

For example, Japanese Patent Application Laid-Open Publication No. 10-143648 discloses the image processing in which a smoothed image obtained by smoothing a digital image is used to form a skeleton of a strip-shaped blood vessel included in the digital image.

SUMMARY OF THE INVENTION

An image processing apparatus according to one aspect of the present invention includes: a region detection section configured to detect a candidate region in which a structure having a predetermined shape is estimated to exist, from an image obtained by image-pickup of a living tissue; a border pixel detection section configured to detect a border pixel corresponding to a border of the candidate region; a region setting section configured to set at least one local region having an area for one or more pixels in each of two neighboring regions located in the vicinity of and both sides of the border pixel; a feature value calculation section configured to calculate predetermined feature values based on predetermined values obtained for respective pixel units in the respective local regions set by the region setting section; a discrimination value calculation section configured to calculate, based on a calculation result of the predetermined feature values in a first local region group set in the neighboring region located on one side when viewed from the border pixel and a calculation result of the predetermined feature values in a second local region group set in the neighboring region located on the other side when viewed from the border pixel, a discrimination value for allowing a difference in the two calculation results of the predetermined feature values to be discriminated; and a candidate region correction section configured to correct a detection result of the candidate region obtained by the region detection section, based on a calculation result of the discrimination value.

An image processing apparatus according to another aspect of the present invention includes: a pixel selection section configured to select a pixel of interest from an image obtained by image-pickup of a living tissue; a region setting section configured to set at least one local region having an area for one or more pixels in each of two neighboring regions located in the vicinity of and both sides of the pixel of interest; a feature value calculation section configured to calculate predetermined feature values based on predetermined values obtained for respective pixel units of the local regions set by the region setting section; a discrimination value calculation section configured to calculate, based on a calculation result of the predetermined feature values in a first local region group set in the neighboring region located on one side when viewed from the pixel of interest and a calculation result of the predetermined feature values in a second local region group in the neighboring region located on the other side when viewed from the pixel of interest, a discrimination value for allowing a difference in the two calculation results of the predetermined feature values to be discriminated; and a candidate region detection section configured to detect a candidate region in which a structure having a predetermined shape is estimated to exist from the image, based on a calculation result of the discrimination value.

An image processing method according to one aspect of the present invention includes: a region detection step of detecting a candidate region in which a structure having a predetermined shape is estimated to exist, from an image obtained by image-pickup of a living tissue; a border pixel detection step of detecting a border pixel corresponding to a border of the candidate region; a region setting step of setting at least one local region having an area for one or more pixels in each of two neighboring regions located in the vicinity of and both sides of the border pixel; a feature value calculation step of calculating predetermined feature values based on predetermined values obtained for respective pixel units of the local regions set in the region setting step; a discrimination value calculation step of calculating, based on a calculation result of the predetermined feature values in a first local region group set in the neighboring region located on one side when viewed from the border pixel and a calculation result of the predetermined feature values in a second local region group set in the neighboring region located on the other side when viewed from the border pixel, a discrimination value for allowing a difference in the two calculation results of the predetermined feature values to be discriminated; and a candidate region correction step of correcting a detection result of the candidate region obtained in the region detection step, based on a calculation result of the discrimination value.

An image processing method according to another aspect of the present invention includes: a pixel selection step of selecting a pixel of interest from an image obtained by image-pickup of a living tissue; a region setting step of setting at least one local region having an area for one or more pixels in each of two neighboring regions located in the vicinity of and both sides of the pixel of interest; a feature value calculation step of calculating predetermined feature values based on predetermined values obtained for respective pixel units of the local regions set in the region setting step; a discrimination value calculation step of calculating, based on a calculation result of the predetermined values in a first local region group set in the neighboring region located on one side when viewed from the pixel of interest and a calculation result of the predetermined feature values in a second local region group in the neighboring region located on the other side when viewed from the pixel of interest, a discrimination value for allowing a difference in the two calculation results of the predetermined feature values to be discriminated; and a candidate region detection step of detecting a candidate region in which a structure having a predetermined shape is estimated to exist from the image, based on a calculation result of the discrimination value.

DETAILED DESCRIPTION OF THE PREFERRED EMBODIMENT(S)

Hereinafter, embodiments of the present invention are described with reference to drawings.

First Embodiment

FIGS. 1 to 11 relate to the first embodiment of the present invention.

Figure 1:
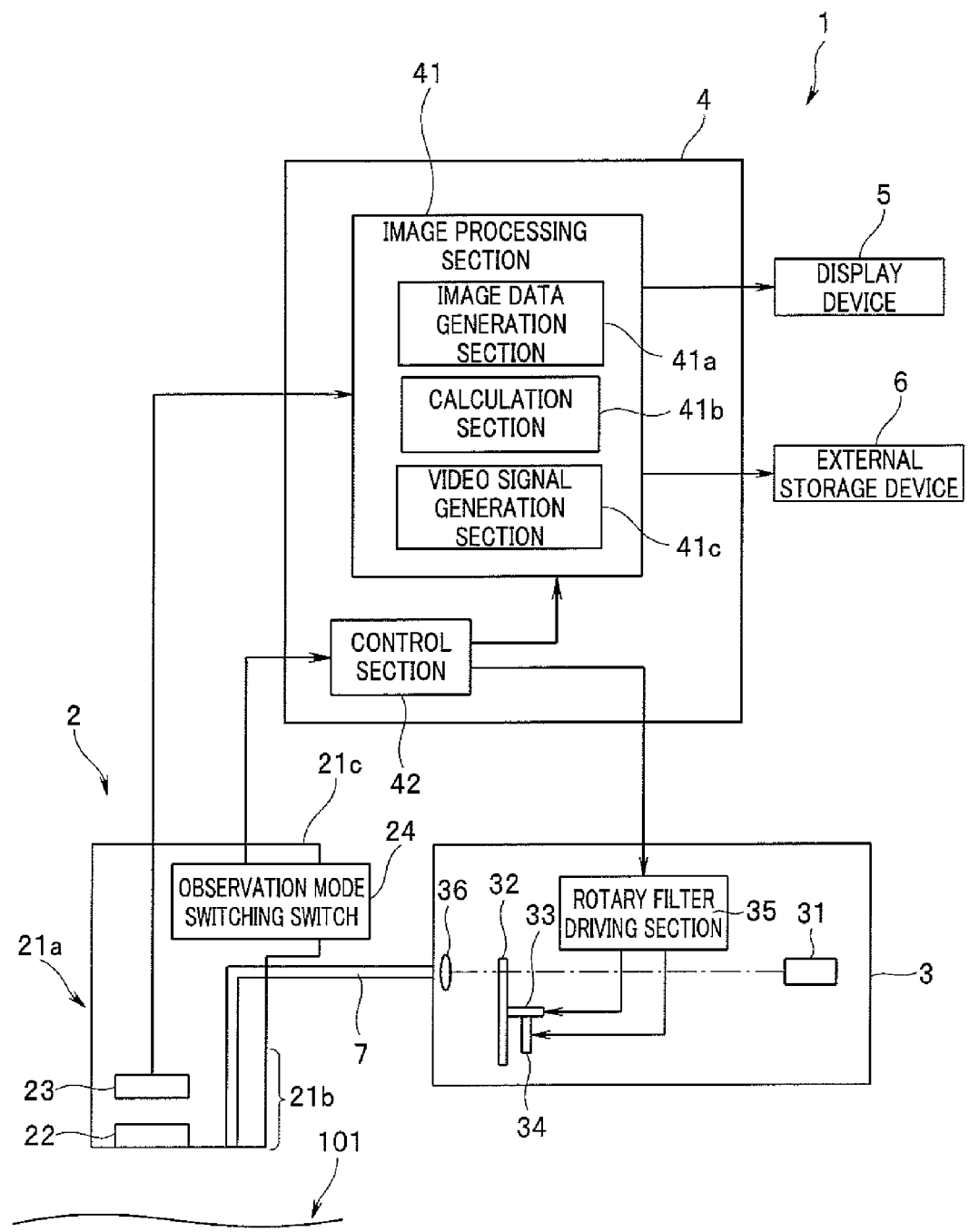
FIG. 1 is a view showing an example of a configuration of a main part of an endoscope apparatus having an image processing apparatus according to an embodiment of the present invention.

As shown in FIG. 1, an endoscope apparatus 1 includes: an endoscope 2 configured to be inserted in a body cavity of a subject to be examined, and to output a signal of an image obtained by picking up an image of an object such as a living tissue 101 in the body cavity; a light source device 3 that emits illumination light to illuminate the living tissue 101; a processor 4 that performs various processings on the signal outputted from the endoscope 2; a display device 5 that displays an image corresponding to a video signal from the processor 4; and an external storage device 6 that stores an output signal corresponding to the processing result in the processor 4.

The endoscope 2 includes an insertion portion 21a having a shape and a dimension insertable in a body cavity of a subject to be examined; a distal end portion 21b provided on a distal end side of the insertion portion 21a; and an operation portion 21c provided on a proximal end side of the insertion portion 21a. In addition, the insertion portion 21a has a light guide 7 inserted therethrough for transmitting the illumination light emitted from the light source device 3 to the distal end portion 21b.

One end surface (light-incident end surface) of the light guide 7 is detachably connected to the light source device 3. In addition, the other end surface (light-emission end surface) of the light guide 7 is arranged in the vicinity of an illumination optical system, not shown, provided at the distal end portion 21b of the endoscope 2. According to such a configuration, the illumination light emitted from the light source device 3 passes through the light guide 7 which is in a state connected to the light source device 3, and the illumination optical system, not shown, provided at the distal end portion 21b, and thereafter emitted to the living tissue 101.

The distal end portion 21b of the endoscope 2 is provided with an objective optical system 22 that forms an optical image of an object, and a CCD 23 that picks up the optical image formed by the objective optical system 22 to obtain an image. Furthermore, the operation portion 21c of the endoscope 2 is provided with an observation mode switching switch 24 through which an instruction for switching an observation mode to either a normal light observation mode or to a narrow-band light observation mode can be given.

The light source device 3 includes: a white light source 31 made of a xenon lamp or the like; a rotary filter 32 that converts white light emitted from the white light source 31 to frame-sequential illumination light; a motor 33 that rotates to drive the rotary filter 32; a motor 34 that causes the rotary filter 32 and the motor 33 to move in a direction perpendicular to the emission optical path of the light source device 31; a rotary filter driving section 35 that drives the motors 33 and 34 based on the control by the processor 4; and a light condensing optical system 36 that condenses the illumination light passed through the rotary filter 32 to supply the condensed illumination light to the incident end surface of the light guide 7.

Figure 2:
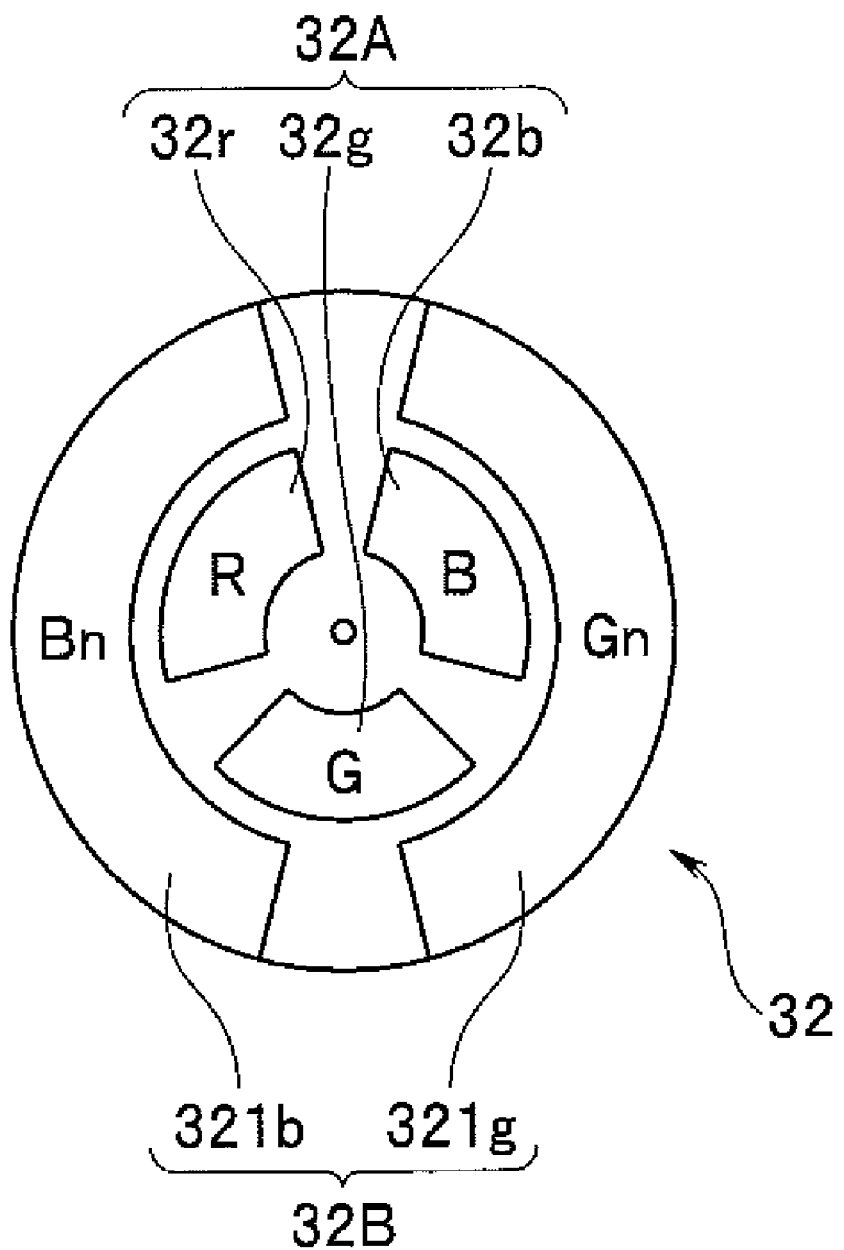
FIG. 2 is a view showing an example of a configuration of a rotary filter included in a light source device in FIG. 1.

As shown in FIG. 2, the rotary filter 32 is configured in a shape of a disk having a rotational axis at the center, and includes a first filter group 32A having a plurality of filters disposed along the circumferential direction on the inner circumferential side, and a second filter group 32B having a plurality of filters disposed along the circumferential direction on the outer circumferential side. The driving force of the motor 33 is transmitted to the rotational axis, and thereby the rotary filter 32 is rotated. Note that the rotary filter 32 is configured of a light-shielding member except for the parts where the first filter group 32A and the second filter group 32B are arranged.

The first filter group 32A includes an R filter 32r for transmitting light in the red wavelength band, a G filter 32g for transmitting light in the green wavelength band, and a B filter 32b for transmitting light in the blue wavelength band, which are respectively arranged along the circumferential direction on the inner circumferential side of the rotary filter 32.

Figure 3:
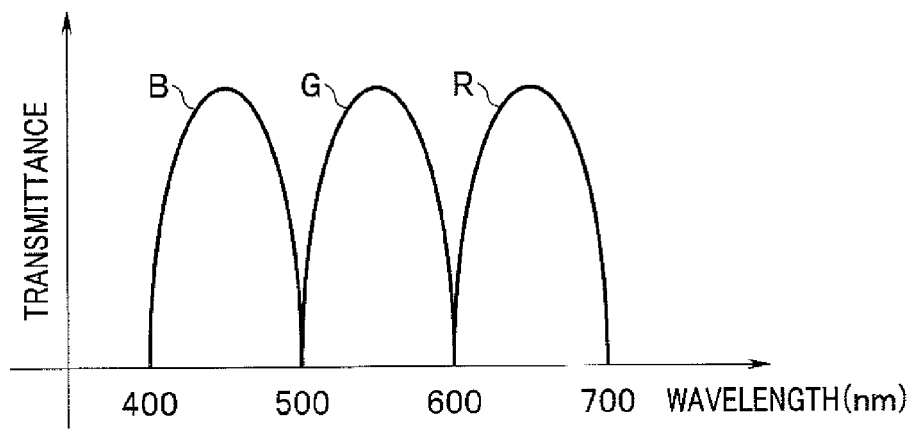
FIG. 3 is a view showing an example of transmission characteristics of respective filters in a first filter group in FIG. 2.

The R filter 32r is configured to transmit light (R light) of wavelengths mainly between 600 nm and 700 nm, as shown in FIG. 3, for example. In addition, the G filter 32g is configured to transmit light (G light) of wavelengths mainly between 500 nm and 600 nm, as shown in FIG. 3, for example. Furthermore, the B filter 32b is configured to transmit light (B light) of wavelengths mainly between 400 nm and 500 nm, as shown in FIG. 3, for example.

That is, the white light emitted from the white light source 31 passes through the first filter group 32A, and thereby broadband light for normal light observation mode is generated.

The second filter group 32B includes a Bn filter 321b for transmitting blue narrow-band light and a Gn filter 32g for transmitting green narrow-band light, which are respectively arranged along the circumferential direction on the outer circumferential side of the rotary filter 32.

Figure 4:
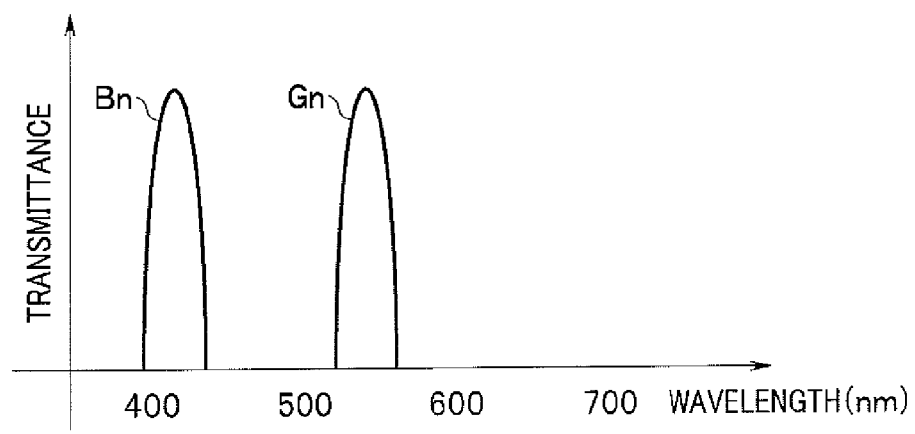
FIG. 4 is a view showing an example of transmission characteristics of respective filters in a second filter group in FIG. 2.

As shown in FIG. 4, for example, the Bn filter 321b is configured to transmit the light (Bn light), the center wavelength of which is set around 415 nm and the wavelength band of which is narrower than that of the B light.

In addition, the Gn filter 321g is configured to transmit the light (Gn light), the center wavelength of which is set around 540 nm and the wavelength band of which is narrower than that of the G light, as shown in FIG. 4, for example.

That is, the white light emitted from the white light source 31 is converted into discrete light by passing through the second filter group 32B, and thereby narrow-band lights of a plurality of wavelengths for narrow-band light observation mode are generated.

The processor 4 includes a function as an image processing apparatus. Specifically, the processor 4 includes an image processing section 41, and a control section 42. In addition, the image processing section 41 includes an image data generation section 41a, a calculation section 41b, and a video signal generation section 41c.

The image data generation section 41a of the image processing section 41 performs processings such as noise removal and A/D conversion on the output signal from the endoscope 2, to generate image data in accordance with the image obtained by the CCD 23, based on the control by the control section 42.

The calculation section 41b of the image processing section 41 performs a predetermined processing using the image data generated by the image data generation section 41a, thereby detecting a predetermined structure such as a blood vessel from the image data. Note that details of the predetermined processing will be described later.

The video signal generation section 41c of the image processing section 41 performs processings such as gamma conversion and D/A conversion on the image data generated by the image data generation section 41a, thereby generating a video signal to output the generated video signal.

When it is detected that an instruction for switching the observation mode to the normal light observation mode has been given based on the instruction by the observation mode switching switch 24, the control section 42 controls the rotary filter driving section 35 so as to cause the light source device 3 to emit broadband light for normal light observation mode. Then, the rotary filter driving section 35 causes the motor 34 to operate such that the first filter group 32A is placed on the emission optical path of the white light source 31 and the second filter group 32B is removed from the emission optical path of the white light source 31, based on the control by the control section 42.

In addition, when it is detected that an instruction for switching the observation mode to the narrow-band light observation mode has been given based on the instruction by the observation mode switching switch 24, the control section 42 controls the rotary filter driving section 35 so as to cause the light source device 3 to emit the narrow-band lights of plurality of wavelength bands for narrow-band light observation mode. Then, the rotary filter driving section 35 operates the motor 34 such that the second filter group 32B is placed on the emission optical path of the white light source 31 and the first filter group 32A is removed from the emission optical path of the white light source 31, based on the control by the control section 42.

That is, according to the configuration of the endoscope apparatus 1 described above, when the normal light observation mode is selected, an image (normal light image) having a color substantially the same as a color in the case where the object is seen with the naked eye can be displayed on the display device 5, and furthermore, the image can be stored in the external storage device 6. In addition, according to the configuration of the endoscope apparatus 1 as described above, when the narrow-band light observation mode is selected, the image (narrow-band light image) on which the blood vessel included in the living tissue 101 is enhanced can be displayed on the display device 5, and furthermore, the image can be stored in the external storage device 6.

Here, the working of the endoscope apparatus 1 will be described.

First, the operator turns on the power source of the components of the endoscope apparatus 1, and thereafter selects the normal light observation mode by the observation mode switching switch 24. Then, the operator inserts the endoscope 2 into the body cavity while viewing the image displayed on the display device 5 when the normal light observation mode is selected, that is, the image having the color substantially the same as the color in the case where the object is seen with the naked eye, thereby bringing the distal end portion 21b close to the region where the living tissue 101 which is an object to be observed exists.

When the normal light observation mode is selected by the observation mode switching switch 24, the respective color lights of R light, G light and B light are sequentially emitted from the light source device 3 to the living tissue 101, and images corresponding to the respective color lights are obtained by the endoscope 2.

Figure 5:
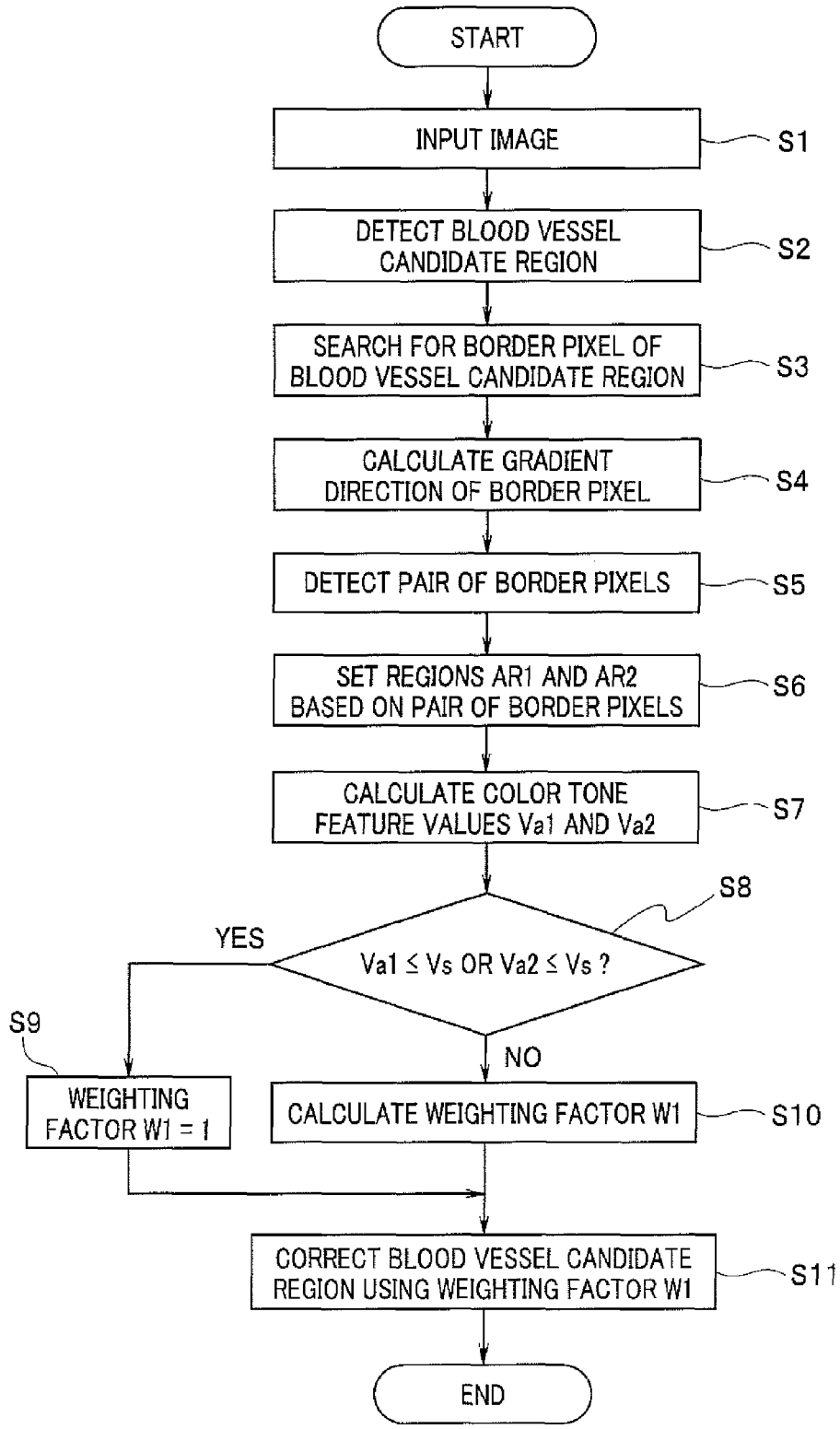
FIG. 5 is a flowchart showing an example of processings performed in a first embodiment of the present invention.

When the image corresponding to the R light, the image corresponding to the G light, and the image corresponding to the B light are inputted, the image data generation section 41a of the image processing section 41 generates image data of color components corresponding to the respective images (step S1 in FIG. 5). Note that, in the present embodiment, for simplification of the description, description will be made supposing that processings will be performed on the image data including blood vessels corresponding to a predetermined structure as an object to be detected, a non-blood-vessel structure such as an edge of the unevenness on the living tissue surface, and a background mucosa, as schematically shown in FIG. 6, for example.

The calculation section 41b having a function of a region detection section performs processings using a publicly known blood vessel detection method on the image data generated by the image data generation section 41a, thereby detecting blood vessel candidate regions as candidate regions where a blood vessel is estimated to exist from the image data (step S2 in FIG. 5), and thereafter temporarily holding the detection result of the blood vessel candidate regions.

Figure 6:
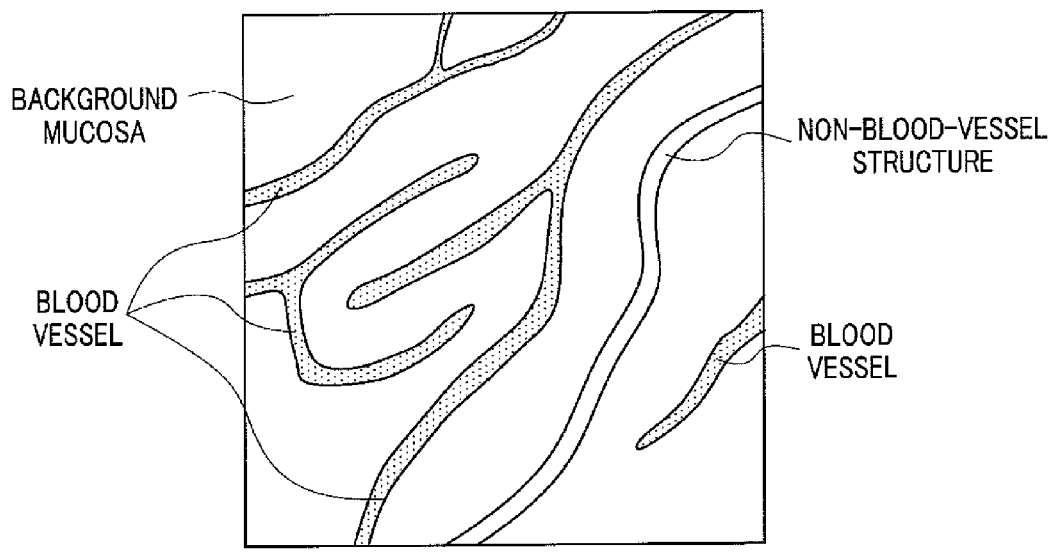
FIG. 6 is a pattern diagram showing an example of image data to be processed.
Figure 7:
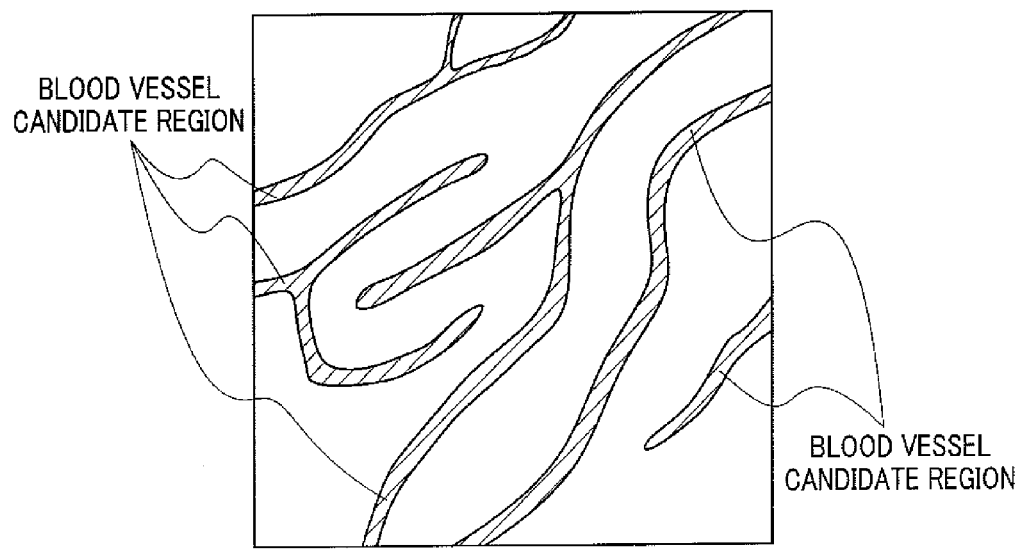
FIG. 7 is a pattern diagram showing an example of detection result of blood vessel candidate regions.

Specifically, the calculation section 41b performs processings using a publicly known blood vessel detection method on the image data schematically shown in FIG. 6, thereby obtaining the detection result of the blood vessel candidate regions as shown in FIG. 7, for example. Note that, in the present embodiment, description will be made supposing that the parts shown by the diagonal line patterns in FIG. 7 are blood vessel candidate regions. Note that, as the publicly known blood vessel detection method for obtaining the above-mentioned detection result, various kinds of methods such as a blood vessel detection method using a band-pass filter or a segment detection method based on a vector concentration degree can be applied, for example.

On the other hand, based on the detection result of the blood vessel candidate regions obtained in the processing in the step S2 in FIG. 5, the calculation section 41b having a function of a border pixel detection section uses a binarized image obtained by performing a threshold processing and the like on the detection result, thereby searching for border pixels corresponding to pixels at edge portions of each of the blood vessel candidate regions (step S3 in FIG. 5).

The calculation section 41b applies a filter such as a Sobel filter to the border pixels obtained in the processing in the step S3 in FIG. 5, to calculate the gradient directions of the border pixels (step S4 in FIG. 5).

The calculation section 41b performs, on the border pixels obtained in the processing in the step S4 in FIG. 5, a processing for detecting two border pixels whose gradient directions form an angle of 180 degrees or approximately 180 degrees and which are located at positions closest to each other as a pair of border pixels (step S5 in FIG. 5).

Based on the pair of border pixels detected in the processing in the step S5 in FIG. 5, the calculation section 41b respectively sets an region AR1 having at the center thereof a pixel which is located at a position away from one of the pair border pixels by a predetermined distance toward the gradient direction, and a region AR2 having at the center thereof a pixel which is located at a position away from the other of the pair of border pixels by the predetermined distance toward the gradient direction (step S6 in FIG. 5).

Figure 8:
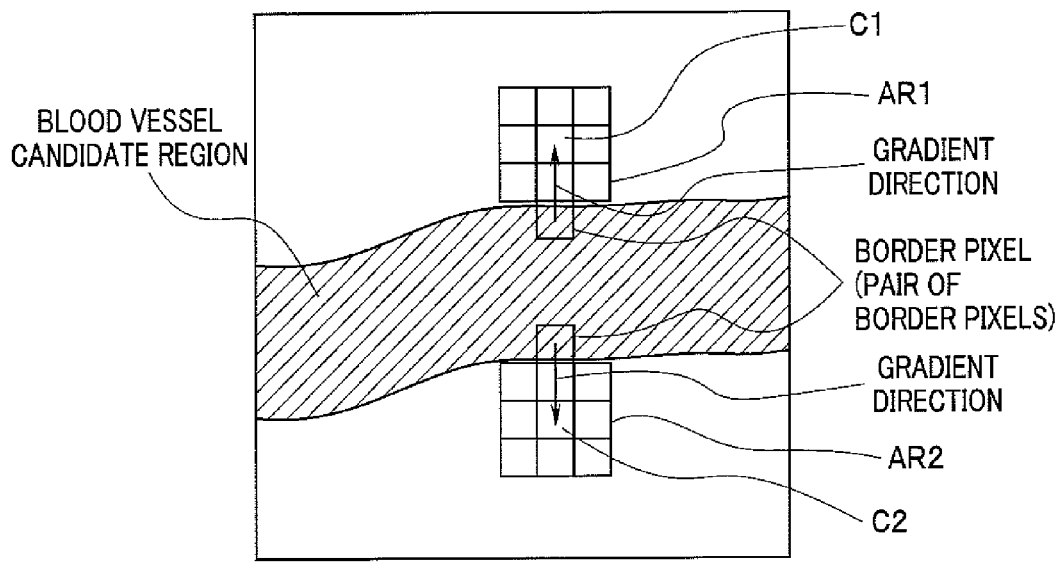
FIG. 8 is a view for illustrating a positional relationship among two border pixels, a region AR1, and a region AR2 in the first embodiment of the present invention.

Specifically, when the above-mentioned predetermined distance is supposed to be the distance for two pixels and both of the regions AR1 and AR2 are the rectangular regions each including 3 times 3 pixels, for example, the positional relationship among the two border pixels constituting one pair of border pixels, the region AR1, and the region AR2 is as schematically shown in FIG. 8.

Note that the region AR1 and the region AR2 may be regions of any shape as long as each of the regions is set as a region having an area for one or more pixels. In addition, a plurality of regions AR1 and a plurality of regions AR2 may be set for one pair of border pixels. Furthermore, the above-mentioned predetermined distance may be an arbitrary distance.

That is, the calculation section 41b having a function of a region setting section sets the regions AR1 and AR2 as local regions each having an area for one or more pixels in two neighboring regions located in the vicinity of and both sides of the one pair of border pixels.

The calculation section 41b having a function of a feature value calculation section calculates a color tone feature value Va1 in the region AR1 and the color tone feature value Va2 in the region AR2 based on the processing result in the step S6 in FIG. 5 (step S7 in FIG. 5).

Specifically, when the pixel value of green color is supposed to be Ga and the pixel value of red color is supposed to be Ra, for example, the calculation section 41b calculates an average value of Ga/Ra values obtained for the respective pixel units set in the region AR1, as the color tone feature value Va1. Furthermore, the calculation section 41b calculates an average value of Ga/Ra values obtained for the respective pixel units set in the region AR2, as the color tone feature value Va2.

Note that the calculation section 41b is not limited to calculate the average value of the Ga/Ra values of the respective pixels as the color tone feature values Va1 and Va2, but may obtain the maximum value of the Ga/Ra values of the respective pixels as the color tone feature values Va1 and Va2, or may obtain the minimum value of the Ga/Ra values of the respective pixels as the color tone feature values Va1 and Va2, for example.

Figure 9:
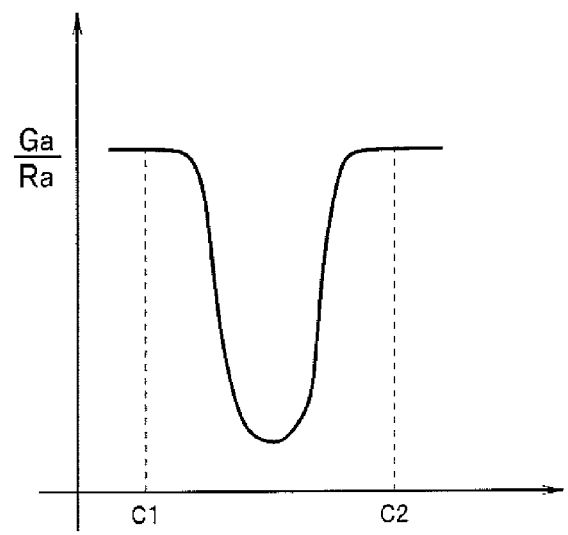
FIG. 9 is a graph showing an example of variation of color tone when a blood vessel is estimated to actually exist in a blood vessel candidate region.
Figure 10:
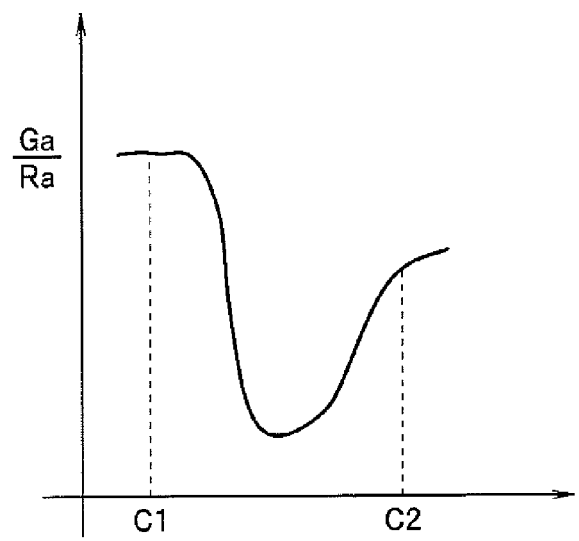
FIG. 10 is a graph showing an example of variation of color tone when a non-blood-vessel structure is estimated to exist in a blood vessel candidate region.

In addition, the calculation section 41b may calculate the color tone feature values Va1 and Va2 using the Ga/Ra value, a pixel value of any one of the color components of R, G, and B, or a luminance value (white/black gradation value) alone, or using plurality of these values in combination, for example, as long as the values showing variations as shown in FIGS. 9 and 10 to be described later are used.

On the other hand, the calculation section 41b calculates the Ga/Ra value of the pixel at the center portion of the blood vessel candidate region which exists between the two border pixels constituting the pair of border pixels, as a color tone feature value Vs. After that, the calculation section 41b determines whether or not the color tone feature value Va1 or the color tone feature value Va2 is equal to or smaller than the color tone feature value Vs (step S8 in FIG. 5).

When obtaining a determination result that at least one of the color tone feature value Va1 and the color tone feature value Va2 is equal to or smaller than the color tone feature value Vs, the calculation section 41b sets a weighting factor W1 in the blood vessel candidate region between the border pixel on the region AR1 side and the border pixel on the region AR2 side to 1 (step S9 in FIG. 5), and thereafter continuously performing the processing in step S11 in FIG. 5. Furthermore, when obtaining the determination result that both of the color tone feature value Va1 and the color tone feature value Va2 are larger than the color tone feature value Vs, the calculation section 41b calculates the weighting factor W1 by performing calculation using the following mathematical expression (1) (step S10 in FIG. 5). Note that when another value (the value of Ra at the pixel at the center portion of the blood vessel candidate region, for example) as the color tone feature value Vs, the weighting factor W1 may be calculated by appropriately reversing the magnitude relation in the determination processing in the step S8 in FIG. 5. Furthermore, according to the present embodiment, the weighting factor W1 may be calculated using a mathematical expression different from the following mathematical expression (1), as long as a mathematical expression in which the maximum value of the weighting factor W1 is obtained if the condition that the color tone feature value Va1 is equal to the color tone feature value Va2 is satisfied is used.

$$W1 = \begin{cases} \dfrac{Va2/Va1 - Thre}{1/Thre} & \text{if } Va1 \geq Va2 \\ \dfrac{Va1/Va2 - Thre}{1/Thre} & \text{if } Va1 < Va2 \end{cases} \quad (1)$$

"Thre" in the above mathematical expression (1) is a threshold set in advance such that Thre is equal to 0.4, for example.

When the Ga/Ra values are sequentially calculated at the pixels from the center C1 of the region AR1 to the center C2 of the region AR2, if the variation of the values as shown in the graph in FIG. 9 is obtained, that is, if almost no difference in the color tones occurs between the region AR1 and the region AR2, a blood vessel is estimated to actually exist in the blood vessel candidate region between the border pixel on the region AR1 side and the border pixel on the region AR2 side.

On the other hand, when the Ga/Ra values are sequentially calculated at the pixels from the center C1 of the region AR1 to the center C2 of the region AR2, if the variation of the values as shown in the graph in FIG. 10 is obtained, that is, a clear difference in the color tones occurs between the region AR1 and the region AR2, a non-blood-vessel structure is estimated to exist in the blood vessel candidate region between the border pixel on the region AR1 side and the border pixel on the region AR2 side.

According to the above mathematical expression (1) constituted using a ratio between the color tone feature value Va1 and the color tone feature value Va2, if the determination condition in the determination processing in the step S8 in FIG. 5 is not satisfied, it is possible to obtain the weighting factor W1 which is a relatively large value when a blood vessel is estimated to actually exist in the blood vessel candidate region between the border pixel on the region AR1 side and the border pixel on the region AR2 side and which is a relatively small value when a non-blood-vessel structure is estimated to exist in the blood vessel candidate.

That is, the calculation section 41b having a function of a discrimination value calculation section calculates, based on the calculation result of the color tone feature value Va1 in the region AR1 and the calculation result of the color tone feature value Va2 in the region AR2, the weighting factor W1 as a discrimination value for allowing the difference in the calculation results of the two color tone feature values to be discriminated.

In addition, also when a pixel corresponding to a bifurcation of a blood vessel is included either in the region AR1 or the region AR2, for example, it is considered that a clear difference in the color tones occurs between the region AR1 and the region AR2. Therefore, when a pixel corresponding to a bifurcation of a blood vessel is included either in the region AR1 or the region AR2, the weighting factor W1 cannot be calculated by the calculation using the above mathematical expression (1). Therefore, in the present embodiment, when the determination condition in the step S8 in FIG. 5 is satisfied, the weighting factor W1 in the blood vessel candidate region between the border pixel on the region AR1 side and the border pixel on the region AR2 side is set to 1, and thereby the detection result of each of the blood vessel candidate regions obtained in the step S2 in FIG. 5 is maintained.

On the other hand, the calculation section 41b having a function of a candidate region correction section corrects the detection result of each of the blood vessel candidate regions obtained in the processing in the step S2 in FIG. 5, by using the weighting factor W1 obtained in the processings in the step S9 and S10 in FIG. 5 (step S11 in FIG. 5).

Specifically, when a detection result in which high evaluation values are uniformly obtained in the pixel groups in the blood vessel candidate regions and low evaluation values are uniformly obtained in the pixel groups in the region other than the blood vessel candidate regions is obtained through the processing in the step S2 in FIG. 5, for example, it is possible to decrease, among the pixel groups which belong to the respective blood vessel candidate regions, the evaluation values of the pixel groups where the non-blood-vessel structures are estimated to exist to a level substantially the same as that of the evaluation values in the region other than the blood vessel candidate regions by superimposing the weighting factor W1 on the detection result (multiplying the detection result by the weighting factor W1).

Figure 11:
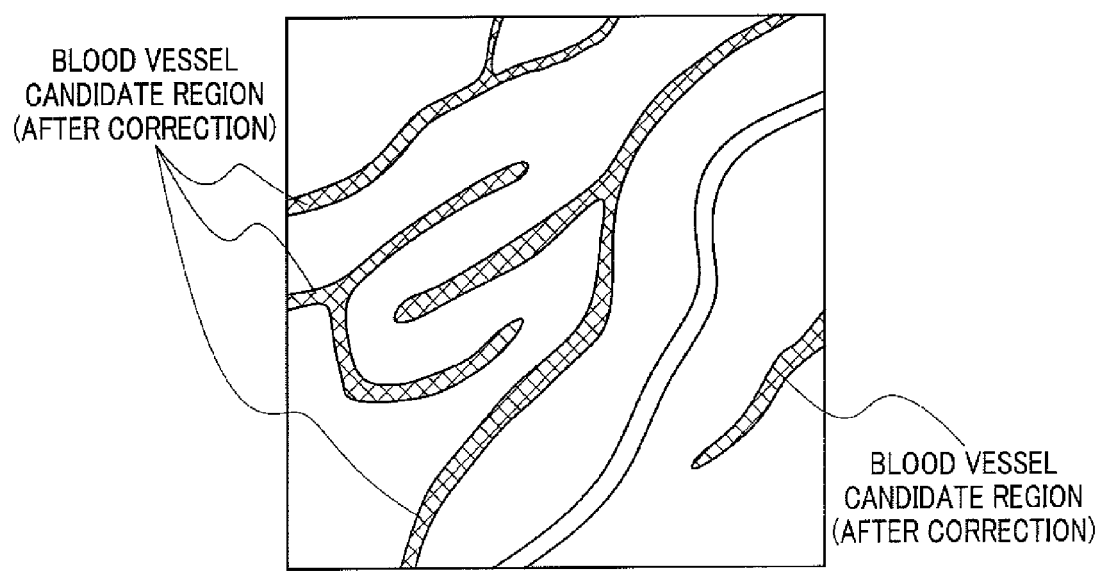
FIG. 11 is a pattern diagram showing an example of a detection result of the blood vessel candidate regions after correction.

Then, the calculation section 41b can obtain the detection result of the blood vessel candidate regions corrected as shown in FIG. 11, for example, as the processing result in the step S11 in FIG. 5.

Therefore, according to the present embodiment, the pixel groups where the non-blood-vessel structures are estimated to exist are included as the detection result of the blood vessel candidate regions, a series of processings shown in FIG. 5 is performed, and thereby capable of correcting the detection result so as to remove the pixel groups as much as possible.

Note that the processings in the present embodiment are not limited to the processings applied only to blood vessels, but can be applied also to a structure other than blood vessels such as pit patterns, for example, in a substantially similar manner. In addition, according to the present embodiment, a processing using an inverse number of the weighting factor W1 obtained through the calculation using the mathematical expression (1) is performed, and thereby capable of detecting an edge of the unevenness on the living tissue surface and a part corresponding to a shadow created due to the unevenness from the image, for example. Therefore, according to the present embodiment, it is possible to improve the detection accuracy of a predetermined structure (such as a blood vessel) included in the image obtained by picking up the image of the living tissue, compared with a conventional method.

In addition, according to the present embodiment, it is not limited to perform the processing for correcting the detection result by applying the weighting factor W1 to the detection result of the blood vessel candidate region obtained by using a publicly known method, but may perform a processing for obtaining the calculation result in which the weighting factor W1 is calculated for each pixel of the image data, as the detection result of the blood vessel candidate regions, for example.

Here, description will be made on a modified example of the present embodiment with reference mainly to FIGS. 12 and 13. Note that subsequent description will be made by appropriately omitting the description of the parts to which the processings substantially the same as those described above can be applied.

Figure 12:
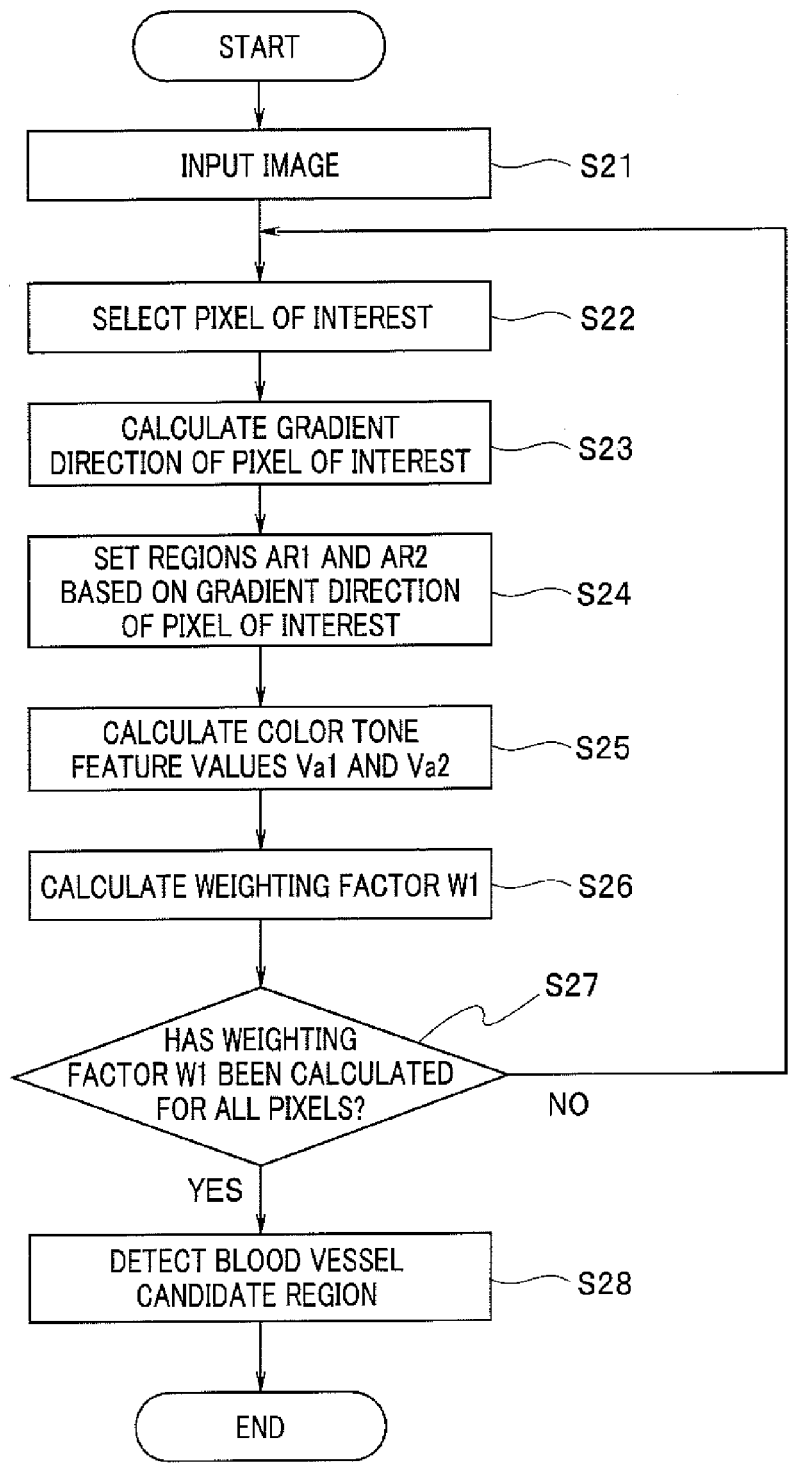
FIG. 12 is a flowchart showing an example of processings performed in a modified example of the first embodiment of the present invention.

When the image corresponding to the R light, the image corresponding to the G light, and the image corresponding to the B light are inputted, the image data generation section 41a of the image processing section 41 generates image data of the color components corresponding to the respective images (step S21 in FIG. 12).

The calculation section 41b having a function of an image selection section selects one pixel of interest from the respective pixels of the image data generated by the image data generation section 41a (step S22 in FIG. 12).

The calculation section 41b applies a filter such as a Sobel filter to the pixel of interest selected in the processing in the step S22, thereby calculating the gradient direction of the pixel of interest (step S23 in FIG. 12).

Based on the gradient direction calculated in the processing in the step S23 in FIG. 12, the calculation section 41b sets the region AR1 having at the center thereof a pixel which is located at the position away from the pixel of interest by a predetermined distance toward the gradient direction, and the region AR2 having at the center thereof a pixel which is located at a position away from the pixel of interest by a predetermined distance toward a direction opposite to the gradient direction (a direction which forms an angle of 180 degrees or approximately 180 degrees with respect to the gradient direction) (step S24 in FIG. 12).

Figure 13:
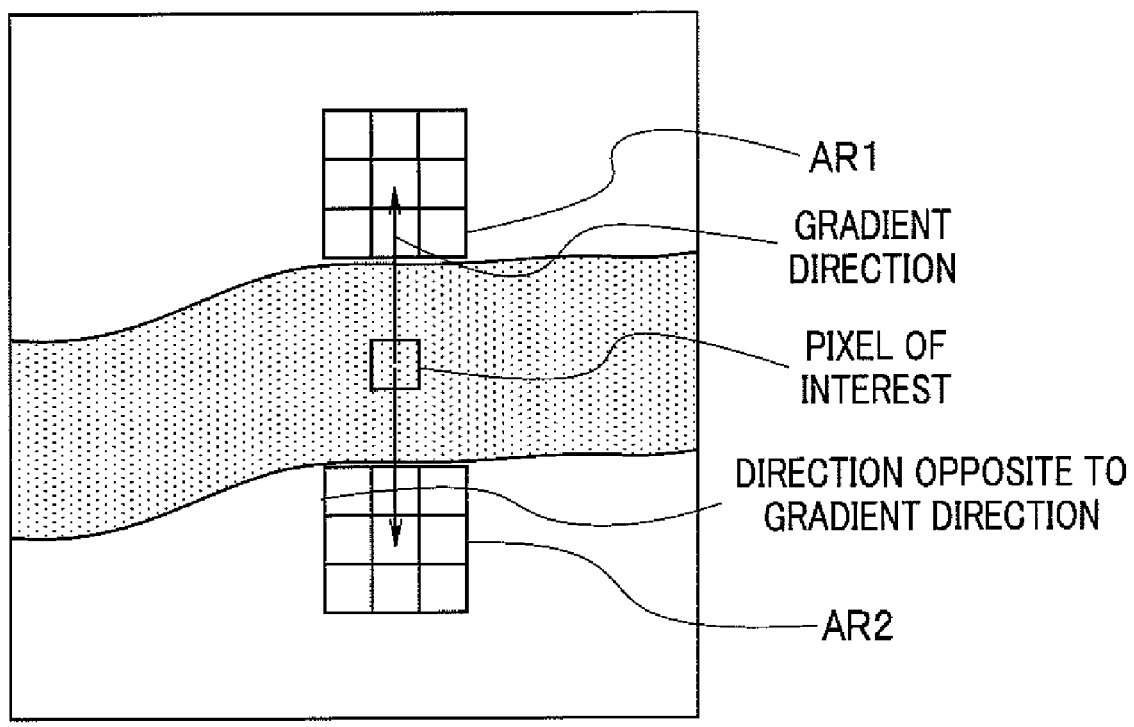
FIG. 13 is a view for illustrating a positional relationship among a pixel of interest, the region AR1, and the region AR2 in the modified example of the first embodiment of the present invention.

Specifically, when the respective regions AR1 and AR2 are rectangular regions each including 3 times 3 pixels, for example, the positional relationship among the pixel of interest, the region AR1, and the region AR2 is as schematically shown in FIG. 13.

That is, the calculation section 41b having a function of a region setting section sets the region AR1 and the region AR2 as local regions each having an area for one or more pixels in two neighboring regions located in the vicinity of and both sides of the pixel of interest.

Based on the processing result in the step S24 in FIG. 12, the calculation section 41b calculates the color tone feature value Va1 in the region AR1 and the color tone feature value Va2 in the region AR2 (step S25 in FIG. 12).

The calculation section 41b calculates the weighting factor W1 by applying the color tone feature values Va1 and Va2 calculated in the step S25 in FIG. 12 to the above-described mathematical expression (1) (step S26 in FIG. 12), and thereafter determining whether or not the weighting factor W1 has been calculated at all of the pixels included in the image data (step S27 in FIG. 12).

After that, the calculation section 41b repeats the processings from the steps S22 to S26 in FIG. 12 until a pixel at which the weighting factor W1 has not been calculated does not exist any more. When the calculation of the weighting factor W1 has been completed at all of the pixels included in the image data, the calculation section 41b having a function of a candidate region detection section detects a group of pixels at which the weighting factor W1 is equal to or larger than a predetermined threshold as the blood vessel candidate region, based on the calculation result of the weighting factor W1 (step S28 in FIG. 12).

Note that the processings in the present modified example are not limited to those applied only to blood vessels, but can be applied to the structure other than blood vessels such as pit patterns, for example, in a substantially similar manner. In addition, according to the present modified example, the processing using an inverse number of the weighting factor W1 obtained through the calculation using the above-described mathematical expression (1) is performed, and thereby capable of detecting an edge of the unevenness on the living tissue surface and a part corresponding to a shadow created due to the unevenness from the image, for example. Therefore, even if the processings according to the present modified example are used instead of the processings according to the above-described embodiment, it is possible to improve the detection accuracy of a predetermined structure (such as a blood vessel) included in the image obtained by picking up the image of the living tissue, compared with a conventional method.

Second Embodiment

FIGS. 14 to 17 relate to the second embodiment of the present invention.

Note that in the present embodiment, processings are performed using an endoscope apparatus 1 having the same configuration as that of the endoscope apparatus 1 in the first embodiment. Therefore, detailed description on the configuration of the endoscope apparatus will be omitted in the present embodiment.

Here, description will be made on the working of the present embodiment. Note that subsequent description will be made by appropriately omitting description of the parts to which the processings substantially the same as those described in the first embodiment can be applied.

Figure 14:
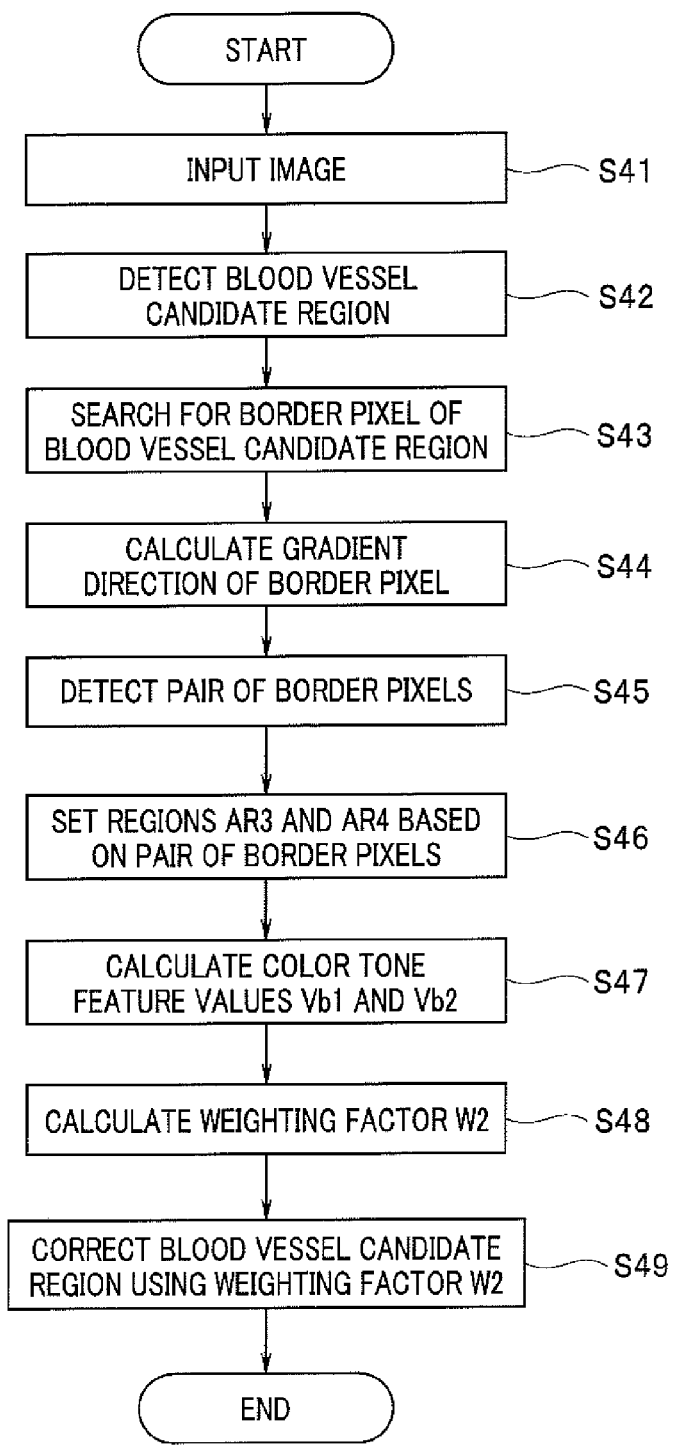
FIG. 14 is a flowchart showing an example of processings performed in a second embodiment of the present invention.

When the image corresponding to the R light, the image corresponding to the G light, and the image corresponding to the B light are inputted, the image data generation section 41a of the image processing section 41 generates image data of the color components corresponding to the respective images (step S41 in FIG. 14). Note that, in the present embodiment, for simplification of the description, description will be made supposing that processings will be performed on the image data including blood vessels corresponding to a predetermined structure as an object to be detected, a non-blood-vessel structure which is an edge of the unevenness on the living tissue surface and the like, and a background mucosa, as schematically shown in FIG. 6, for example.

The calculation section 41b performs a processing using a publicly known blood vessel detection method on the image data generated by the image data generation section 41a, thereby detecting blood vessel candidate regions as a candidate regions where blood vessels are estimated to exist from the image data (step S42 in FIG. 14), and thereafter temporarily holding the detection result of the blood vessel candidate regions.

Specifically, the calculation section 41b performs processing using a publicly known blood vessel detection method on the image data schematically shown in FIG. 6, thereby obtaining the detection result of the blood vessel candidate regions as shown in FIG. 7, for example. Note that, in the present embodiment, description will be made supposing that the parts shown by the diagonal line patterns in FIG. 7 are blood vessel candidate regions. Note that, as the publicly known blood vessel detection method for obtaining the above-mentioned detection result, various kinds of methods such as a blood vessel detection method using a band-pass filter or a segment detection method based on a vector concentration degree can be applied, for example.

On the other hand, based on the detection result of the blood vessel candidate regions obtained in the processing in the step S42 in FIG. 14, the calculation section 41b uses a binarized image obtained by performing a threshold processing and the like on the detection result, thereby searching for border pixels corresponding to pixels at the edge portions of each of the blood vessel candidate regions (step S43 in FIG. 14).

The calculation section 41b applies a filter such as a Sobel filter to the border pixels obtained in the processing in the step S43 in FIG. 14, to calculate the gradient directions of the border pixels (step S44 in FIG. 14).

The calculation section 41b performs, on the border pixels obtained in the processing in the step S44 in FIG. 14, a processing for detecting two border pixels whose gradient directions form an angle of 180 degrees or approximately 180 degrees and which are located at positions closest to each other as a pair of border pixels (step S45 in FIG. 14).

Based on the pair of border pixels detected in the processing in the step S45 in FIG. 14, the calculation section 41b respectively sets an region AR3 having at the center thereof a pixel which is located at a position away from one of the pair of border pixels by a predetermined distance toward the gradient direction, and a region AR4 having at the center thereof a pixel which is located at a position away from the other of the pair of border pixels by the predetermined distance toward the gradient direction (step S46 in FIG. 14).

Figure 15:
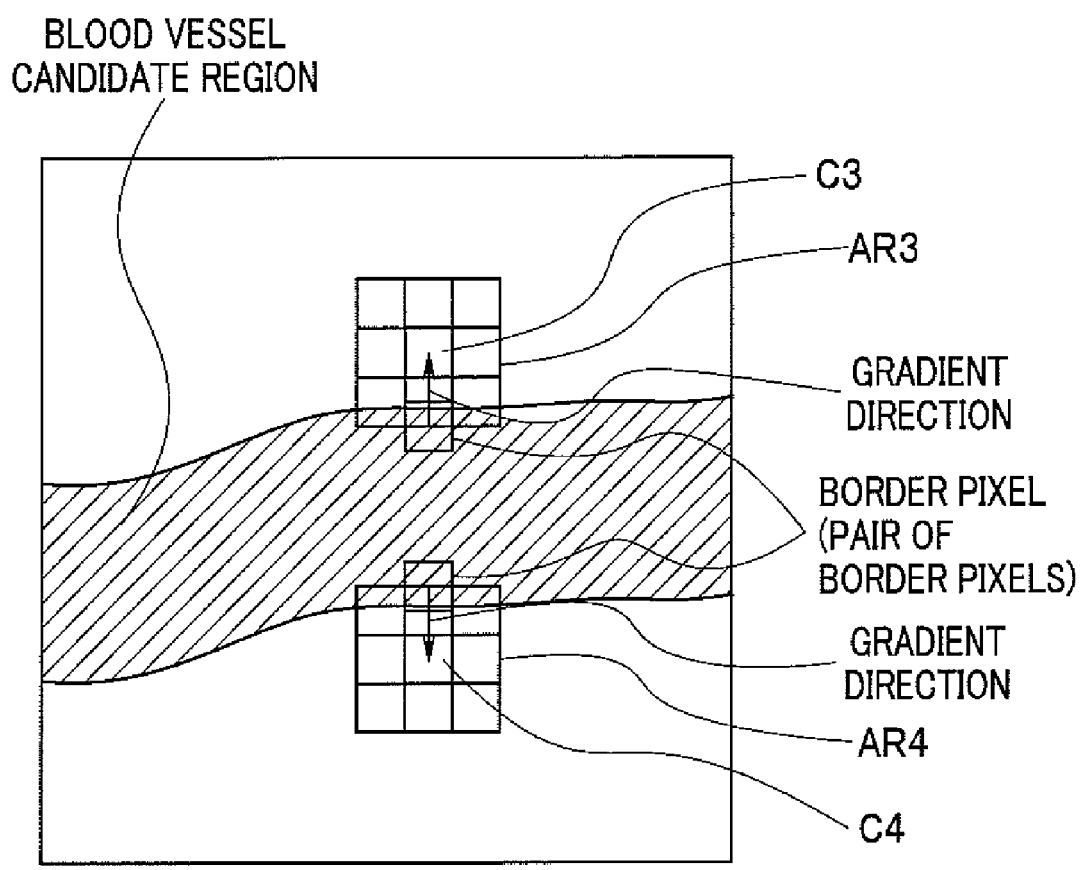
FIG. 15 is view for illustrating a positional relationship among two border pixels, a region AR3, and a region AR4 in the second embodiment of the present invention.

Specifically, when the above-mentioned predetermined distance is estimated to be the distance for 1.5 pixels and both of the regions AR3 and AR4 are the rectangular regions each including 3 times 3 pixels, for example, the positional relationship among the two border pixels constituting one pair of border pixels, the region AR3, and the region AR4 is as schematically shown in FIG. 15.

Note that the region AR3 and the region AR4 may be regions of any shape as long as each of the regions is set as a region having an area for one or more pixels and including at least a part of the border pixels. (The regions AR3 and AR4 shown in FIG. 15 are described by taking a case in which each of the regions is set so as to include the border pixel by 0.5 pixel in the rectangular region including 3 times 3 pixels as an example.) In addition, a plurality of regions AR3 and a plurality of regions AR4 may be set for one pair of border pixels. Furthermore, the above-mentioned predetermined distance may be an arbitrary distance as long as a part of the one of the border pixels is included in the region AR3 and a part of the other of the border pixels is included in the region AR4.

That is, the calculation section 41b having a function of a region setting section sets the regions AR3 and AR4 as local regions each having an area for one or more pixels in two neighboring regions located in the vicinity of and both sides of the one pair of border pixels.

The calculation section 41b having a function of a feature value calculation section calculates a gradient feature value Vb1 in the region AR3 and the gradient feature value Vb2 in the region AR4 based on the processing result in the step S46 in FIG. 14 (step S47 in FIG. 14).

Specifically, the calculation section 41b calculates an average value of the gradient strengths obtained by applying the Sobel filter to the respective pixel units set in the region AR3, as a gradient feature value Vb1, for example. In addition, the calculation section 41b calculates an average value of the gradient strengths obtained by applying the Sobel filter to the respective pixel units set in the region AR4, as a gradient feature value Vb2, for example.

Note that the calculation section 41b is not limited to obtain the gradient strengths by applying the Sobel filter to the respective pixel units, but may obtain the gradient strengths for the respective pixel units by using another method.

On the other hand, the calculation section 41b applies the gradient feature values Vb1 and Vb2 obtained in the processing in the step S47 in FIG. 14 to the following mathematical expression (2), thereby calculating a weighting factor W2 (step S48 in FIG. 14). Note that, according to the present embodiment, the weighting factor W2 may be calculated by using a mathematical expression different from the following mathematical expression (2), as long as a mathematical expression in which the maximum value of the weighting factor W2 is obtained if the condition that the gradient feature value Vb1 is equal to the gradient feature value Vb2 is satisfied is used.

$$W2 = \frac{2}{Vb1/Vb2 + Vb2/Vb1} \quad (2)$$

Figure 16:
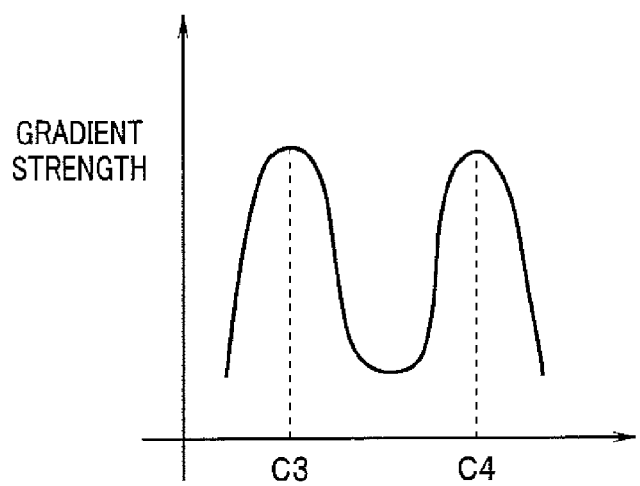
FIG. 16 is a graph showing an example of variation of gradient strength when a blood vessel is estimated to actually exist in a blood vessel candidate region.

When the gradient strengths are sequentially calculated at pixels from the center C3 of the region AR3 to the center C4 of the region AR4, if the variation of the values as shown in the graph in FIG. 16 is obtained, that is, if almost no difference in the gradient strengths occurs between the region AR3 and the region AR4, a blood vessel is estimated to actually exist in the blood vessel candidate region between the border pixel on the region AR3 side and the border pixel on the region AR4 side.

Figure 17:
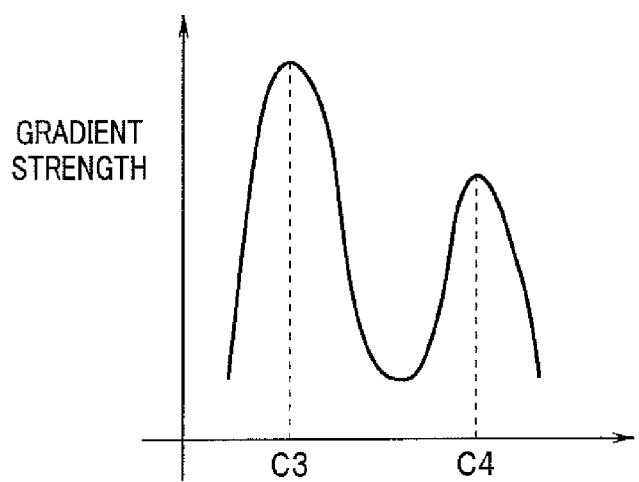
FIG. 17 is a graph showing an example of variation of gradient strength when a non-blood-vessel structure is estimated to exist in a blood vessel candidate region.

On the other hand, when the gradient strengths are sequentially calculated at pixels from the center C3 of the region AR3 to the center C4 of the region AR4, if the variation of the values as shown in the graph in FIG. 17 is obtained, that is, a clear difference in the gradient strengths occurs between the region AR3 and the region AR4, a non-blood-vessel structure is estimated to exist in the blood vessel candidate region between the border pixel on the region AR3 side and the border pixel on the region AR4 side.

According to the above mathematical expression (2) constituted using the ratio between the gradient feature value Vb1 and the gradient feature value Vb2, it is possible to obtain the weighting factor W2 which is a relatively large value when a blood vessel is estimated to actually exist in the blood vessel candidate region between the border pixel on the region AR3 side and the border pixel on the region AR4 side, and which is a relatively small value when a non-blood-vessel structure is estimated to exist in the blood vessel candidate region.

That is, the calculation section 41b having a function of a discrimination value calculation section calculates, based on the calculation result of the gradient feature value Vb1 in the region AR3 and the calculation result of the gradient feature value Vb2 in the region AR4, the weighting factor W2 as a discrimination value for allowing the difference in the calculation results of the two gradient feature values to be discriminated.

The calculation section 41b having a function of a candidate region correction section corrects the detection result of each of the blood vessel candidate regions obtained in the processing in the step S42 in FIG. 14, by using the weighting factor W2 obtained in the processing in the step S48 in FIG. 14 (step S49 in FIG. 14).

Specifically, when a detection result in which high evaluation values are uniformly obtained in the pixel groups in the blood vessel candidate regions and low evaluation values are uniformly obtained in the pixel groups in the region other than the blood vessel candidate regions is obtained through the processing in the step S42 in FIG. 14, for example, it is possible to decrease, among the pixel groups which belong to the respective blood vessel candidate regions, the evaluation value of the pixel group where the non-blood-vessel structure is estimated to exist to a level substantially the same as that of the evaluation values in the region other than the blood vessel candidate regions by superimposing the weighting factor W2 on the detection result (multiplying the detection result by the weighting factor W2).

Then, the calculation section 41b can obtain the detection result of the blood vessel candidate regions corrected as shown in FIG. 11, for example, as the processing result in the step S49 in FIG. 14.

Therefore, according to the present embodiment, the pixel groups where the non-blood-vessel structures are estimated to exist are included as the detection result of the blood vessel candidate regions, a series of processings shown in FIG. 14 is performed, and thereby capable of correcting the detection result so as to remove the pixel groups as much as possible.

Note that the processings in the present embodiment are not limited to those applied only to blood vessels, but can be applied also to the structure other than blood vessels such as pit patterns, for example, in a substantially similar manner. In addition, according to the present modified example, the processing using an inverse number of the weighting factor W2 obtained through the calculation using the above-described mathematical expression (2) is performed, and thereby capable of detecting an edge of the unevenness on the living tissue surface and a part corresponding to a shadow created due to the unevenness from the image, for example. Therefore, according to the present embodiment, it is possible to improve the detection accuracy of a predetermined structure (such as a blood vessel) included in the image obtained by picking up the image of the living tissue, compared with a conventional method.

The present invention is not limited to the above-described embodiments and it is needless to say that various changes and modifications can be made without departing from the scope of the present invention.

What is claimed is:

1. An image processing apparatus comprising:
a region detection section configured to detect a candidate region in which a structure having a predetermined shape is estimated to exist, from an image obtained by image-pickup of a living tissue;
a border pixel detection section configured to detect a border pixel corresponding to a border of the candidate region;
a region setting section configured to set at least one local region having an area for one or more pixels in each of two neighboring regions located in the vicinity of and both sides of the border pixel;
a feature value calculation section configured to calculate predetermined feature values based on predetermined values obtained for respective pixel units in the respective local regions set by the region setting section;
a discrimination value calculation section configured to calculate, based on a calculation result of the predetermined feature values in a first local region group set in the neighboring region located on one side when viewed from the border pixel and a calculation result of the predetermined feature values in a second local region group set in the neighboring region located on the other side when viewed from the border pixel, a discrimination value for allowing a difference in the two calculation results of the predetermined feature values to be discriminated; and
a candidate region correction section configured to correct a detection result of the candidate region obtained by the region detection section, based on a calculation result of the discrimination value.

2. The image processing apparatus according to claim 1, wherein the first local region group and the second local region group are respectively set based on a gradient direction of the border pixel.

3. The image processing apparatus according to claim 1, wherein the feature value calculation section calculates each of the predetermined feature values based on at least one of a pixel value, a ratio of pixel values, a luminance value, and a gradient strength obtained for each of the respective pixel units of the local regions set by the region setting section.

4. The image processing apparatus according to claim 1, wherein the feature value calculation section calculates one of an average value, a maximum value, and a minimum value of the predetermined values as each of the predetermined feature values.

5. The image processing apparatus according to claim 1, wherein the predetermined shape is a linear shape.

6. An image processing apparatus comprising:
a pixel selection section configured to select a pixel of interest from an image obtained by image-pickup of a living tissue;
a region setting section configured to set at least one local region having an area for one or more pixels in each of two neighboring regions located in the vicinity of and both sides of the pixel of interest;
a feature value calculation section configured to calculate predetermined feature values based on predetermined values obtained for respective pixel units of the local regions set by the region setting section;
a discrimination value calculation section configured to calculate, based on a calculation result of the predetermined feature values in a first local region group set in the neighboring region located on one side when viewed from the pixel of interest and a calculation result of the predetermined feature values in a second local region group in the neighboring region located on the other side when viewed from the pixel of interest, a discrimination value for allowing a difference in the two calculation results of the predetermined feature values to be discriminated; and
a candidate region detection section configured to detect a candidate region in which a structure having a predetermined shape is estimated to exist from the image, based on a calculation result of the discrimination value.

7. The image processing apparatus according to claim 6, wherein the first local region group and the second local region group are respectively set based on a gradient direction of the pixel of interest.

8. The image processing apparatus according to claim 6, wherein the feature value calculation section calculates each of the predetermined feature values based on at least one of a pixel value, a ratio of pixel values, a luminance value, and a gradient strength obtained for each of the respective pixel units of the local regions set by the region setting section.

9. The image processing apparatus according to claim 6, wherein the feature value calculation section calculates one of an average value, a maximum value, and a minimum value of the predetermined values as each of the predetermined feature values.

10. The image processing apparatus according to claim 6, wherein the predetermined shape is a linear shape.

11. A method of controlling an image processing apparatus for detecting a structure having a predetermined shape with respect to a medical image, the method comprising:
a region detection step of a region detection section detecting a candidate region in which a structure having a predetermined shape is estimated to exist, from an image obtained by image-pickup of a living tissue;
a border pixel detection step of a border pixel detection section detecting a border pixel corresponding to a border of the candidate region;
a region setting step of a region setting section setting at least one local region having an area for one or more pixels in each of two neighboring regions located in the vicinity of and both sides of the border pixel;
a feature value calculation step of a feature value calculation section calculating predetermined feature values based on predetermined values obtained for respective pixel units of the local regions set in the region setting step;
a discrimination value calculation step of a discrimination value calculation section calculating, based on a calculation result of the predetermined feature values in a first local region group set in the neighboring region located on one side when viewed from the border pixel and a calculation result of the predetermined feature values in a second local region group set in the neighboring region located on the other side when viewed from the border pixel, a discrimination value for allowing a difference in the two calculation results of the predetermined feature values to be discriminated; and
a candidate region correction step of a candidate region correction section correcting a detection result of the candidate region obtained in the region detection step, based on a calculation result of the discrimination value.

12. The method of controlling an image processing apparatus according to claim 11, wherein the first local region group and the second local region group are respectively set based on a gradient direction of the border pixel.

13. The method of controlling an image processing apparatus according to claim 11, wherein, in the feature value calculation step, each of the predetermined feature values is calculated based on at least one of a pixel value, a ratio of pixel values, a luminance value, and a gradient strength obtained for each of the respective pixel units of the local regions set in the region setting step.

14. The method of controlling an image processing apparatus according to claim 11, wherein, in the feature value calculation step, one of an average value, a maximum value, and a minimum value of the predetermined values is calculated as each of the predetermined feature values.

15. The method of controlling an image processing apparatus according to claim 11, wherein the predetermined shape is a linear shape.

16. A method of controlling an image processing apparatus for detecting a structure having a predetermined shape with respect to a medical image, the method comprising:

a pixel selection step of a pixel selection section selecting a pixel of interest from an image obtained by image-pickup of a living tissue;

a region setting step of a region setting section setting at least one local region having an area for one or more pixels in each of two neighboring regions located in the vicinity of and both sides of the pixel of interest;

a feature value calculation step of a feature value calculation section calculating predetermined feature values based on predetermined values obtained for respective pixel units of the local regions set in the region setting step;

a discrimination value calculation step of a discrimination value calculation section calculating, based on a calculation result of the predetermined values in a first local region group set in the neighboring region located on one side when viewed from the pixel of interest and a calculation result of the predetermined feature values in a second local region group in the neighboring region located on the other side when viewed from the pixel of interest, a discrimination value for allowing a difference in the two calculation results of the predetermined feature values to be discriminated; and a candidate region detection step of a candidate region detection section detecting a candidate region in which a structure having a predetermined shape is estimated to exist from the image, based on a calculation result of the discrimination value.

17. The method of controlling an image processing apparatus according to claim 16, wherein the first local region group and the second local region group are respectively set based on a gradient direction of the pixel of interest.

18. The method of controlling an image processing apparatus according to claim 16, wherein, in the feature value calculation step, each of the predetermined feature values is calculated based on at least one of a pixel value, a ratio of pixel values, a luminance value, and a gradient strength obtained for each of the respective pixel units of the local regions set in the region setting step.

19. The method of controlling an image processing apparatus according to claim 16, wherein, in the feature value calculation step, one of an average value, a maximum value, and a minimum value of the predetermined values is calculated as each of the predetermined feature values.

20. The method of controlling an image processing apparatus according to claim 16, wherein the predetermined shape is a linear shape.

\* \* \* \* \*